(12) United States Patent
Tabbaa et al.

(10) Patent No.: US 10,970,789 B2
(45) Date of Patent: Apr. 6, 2021

(54) SYSTEMS AND METHODS FOR FACILITATING INSURANCE COVERAGE

(71) Applicant: SymplexBio Consulting, LLC, Flagstaff, AZ (US)

(72) Inventors: Suzanne Tabbaa, Fort Collins, CO (US); Christian Bezenar, Parker, CO (US)

(73) Assignee: Full Circle Innovation LLC, Flagstaff, AZ (US)

( * ) Notice: Subject to any disclaimer, the term of this patent is extended or adjusted under 35 U.S.C. 154(b) by 0 days.

(21) Appl. No.: 16/252,331

(22) Filed: Jan. 18, 2019

(65) Prior Publication Data
US 2019/0228473 A1 Jul. 25, 2019

Related U.S. Application Data

(60) Provisional application No. 62/620,761, filed on Jan. 23, 2018.

(51) Int. Cl.
*G06Q 40/08* (2012.01)
*G16H 15/00* (2018.01)

(52) U.S. Cl.
CPC .............. *G06Q 40/08* (2013.01); *G16H 15/00* (2018.01)

(58) Field of Classification Search
CPC ................................ G06Q 40/08; G16H 15/00
See application file for complete search history.

(56) References Cited

U.S. PATENT DOCUMENTS

| | | | |
|---|---|---|---|
| 6,409,730 B1 | 6/2002 | Green et al. | |
| 6,440,444 B2 | 8/2002 | Boyce et al. | |
| 6,915,254 B1 | 7/2005 | Heinze et al. | |
| 7,725,330 B2 | 5/2010 | Rao et al. | |
| 7,828,853 B2 | 11/2010 | Ek et al. | |
| 7,860,812 B2 | 12/2010 | Hartley et al. | |
| 8,597,362 B2 | 12/2013 | Shenoy et al. | |
| 8,612,261 B1 | 12/2013 | Swanson et al. | |
| 8,679,123 B2 | 3/2014 | Kinmon et al. | |
| 8,690,956 B2 | 4/2014 | Cook et al. | |
| 9,370,428 B2 | 6/2016 | Winslow et al. | |
| 9,622,871 B2 | 4/2017 | Sander | |
| 10,474,792 B2 | 11/2019 | Alstad et al. | |
| 2002/0082863 A1* | 6/2002 | Kleinke | G16H 40/67 705/2 |
| 2003/0171953 A1 | 9/2003 | Narayanan et al. | |

(Continued)

OTHER PUBLICATIONS

Scott Herbst, 3 Key Areas An Automated Prior Authorization Solution Must Address, hitconsultant.net (Year: 2017).*

(Continued)

*Primary Examiner* — Sarah M Monfeldt
*Assistant Examiner* — Brock E Turk
(74) *Attorney, Agent, or Firm* — Diederiks & Whitelaw, PLC.

(57) ABSTRACT

Electronically generated information for facilitating the efficient and effective authorization of a medical procedure, treatment or medicine are provided. The information is specific to a patient's insurance company, medical need and diagnosis. An electronic Database has been configured for analysis by a user such that inputs to the Database result in outputs considered necessary in a preparation and submission for authorization of the medical procedure, treatment or medicine.

14 Claims, 2 Drawing Sheets

(56) References Cited

U.S. PATENT DOCUMENTS

| | | | |
|---|---|---|---|
| 2004/0249665 A1* | 12/2004 | David | G06Q 40/08 |
| | | | 705/2 |
| 2005/0137910 A1 | 6/2005 | Rao et al. | |
| 2006/0122864 A1* | 6/2006 | Gottesman | G06F 19/3418 |
| | | | 705/2 |
| 2011/0166875 A1 | 7/2011 | Hayter et al. | |
| 2011/0246225 A1* | 10/2011 | Green, III | G06F 19/328 |
| | | | 705/2 |
| 2011/0257756 A1 | 10/2011 | Strzepa et al. | |
| 2013/0332194 A1 | 12/2013 | D'Auria et al. | |
| 2014/0100864 A1 | 4/2014 | Matosich | |
| 2014/0195265 A1 | 7/2014 | Kings et al. | |
| 2014/0278528 A1* | 9/2014 | Simha | G06F 19/328 |
| | | | 705/3 |
| 2014/0350688 A1 | 11/2014 | Michel et al. | |
| 2015/0112727 A1* | 4/2015 | Baym | G06Q 40/08 |
| | | | 705/4 |
| 2016/0283676 A1* | 9/2016 | Lyon | G06Q 10/10 |
| 2016/0321410 A1 | 11/2016 | Timmerman et al. | |
| 2017/0046491 A1 | 2/2017 | Scantland et al. | |
| 2019/0172572 A1 | 6/2019 | Piron et al. | |
| 2019/0228473 A1 | 7/2019 | Tabbaa et al. | |

OTHER PUBLICATIONS

British Columbia Ministry of Health, TELEPLAN Electronic Medical Claims System, Aug. 2016, pp. 1-163 (Year: 2016).*

Bugbee et al., "Bipolar Fresh Osteochondral Allografting of the Tibiotalar Joint," *The Journal of Bone & Joint Surgery*, vol. 95-A, No. 5, Mar. 6, 2013, pp. 426-432.

Bugbee et al., "Osteochondral Allograft Transplantation in Cartilage Repair: Graft Storage Paradigm, Translational Models, and Clinical Applications," Journal of Orthopaedic Research, Jan. 2016, pp. 31-38.

Makino et al., "The Effect of Graft Sizing on Osteochondral Transplantation," *Arthroscopy*, Oct. 2004, 20:8, pp. 837-840.

U.S. Appl. No. 16/002,662, filed Jun. 7, 2018, Mologne et al.

U.S. Appl. No. 16/287,992, filed Feb. 27, 2019, Cerundolo et al.

* cited by examiner

SYSTEMS AND METHODS FOR FACILITATING INSURANCE COVERAGE

CROSS-REFERENCE TO RELATED APPLICATION

This application claims the benefit under 35 U.S.C. § 119(e) of U.S. Provisional Patent Application No. 62/620,761, filed on Jan. 23, 2018, and entitled "Systems and Methods for Facilitating Insurance Coverage," the contents of which are incorporated by reference as if fully disclosed herein.

FIELD OF THE INVENTION

Systems and methods for facilitating insurance coverage for patients in need of a medical procedure, treatment or medication.

BACKGROUND OF THE INVENTION

Health care reimbursement by insurance companies is of particular concern to health care providers and end-users in need of timely medical assistance. This is true where the medical assistance is a surgical repair, medical implant, cancer treatment, pharmaceutical, prosthetic or any other necessitated procedure, treatment or medicine. The patient's health care provider will typically prepare and submit information required by an insurance company to determine whether coverage will be granted for the particular medical patient need. Importantly, the information useful for reimbursement of a medical procedure, for example, from one insurance company is often different than the information necessitated by a different insurance company. As such, the reimbursement process is often time consuming and burdensome on the patient and the health care provider, typically resulting in some level of hindrance in a patient's sought after medical assistance.

In addition, insurance companies will often request additional follow-up materials during the approval process which further delays their decision. If coverage is denied, additional time and cost is required for an appeals process. The result is that medical coverage is delayed for the patient until the procedure, treatment or medicine is approved by the insurance company, or the patient is denied coverage and forced to pay out of pocket. In some cases, the patient is simply forced to forego the medical procedure, treatment or medicine in place of other less costly or other covered alternatives.

Health care providers spend significant time attempting to obtain approval for patients in need of medical assistance. In one recent study undertaken by the Inventors, health care providers estimated they spent upwards of 4 hours per patient in preparing and submitting prior-authorization paperwork for a medical implant procedure, and upwards of 10 hours per patient when the patient was denied coverage, and an appeal of the negative decision required. In addition, preparation delays and claim denials can result in negative outcomes for the patient, such that a denial can lead to the patient being in pain during the period of delay, a possible decreased likelihood for the medical procedures success, and/or payment out of pocket. There is a need in the industry to facilitate the potential for insurance coverage approval, as well as to make the overall process more time efficient and reduce cost (for the health care provider and for the insurance company).

Against this backdrop the current disclosure is provided.

SUMMARY OF INVENTION

Embodiments herein assist health care providers or other users in the efficient and effective pursuit of coverage from an insurance company for medical procedures, treatments or medicines.

In embodiments herein, systems and methods for assisting a user in obtaining approval of coverage for a medical procedure, treatment or medicine from an insurance company are provided. In one aspect, a patient visits a health care provider and patient specific health care information is obtained. Based on the patient specific health care information, the user searches an electronic Database with inputs, termed "user inputs" herein. In some cases, the user inputs include at least the identity of the insurance company and medical procedure in need of coverage. In other cases, user inputs can include the patient's diagnosis, the patient's specific health care information, and/or details obtained from the patient's insurance policy. Outputs, termed "system outputs," that are important in assisting the user in preparing and submitting materials/information for the approval process are identified and provided to the user by an electronic Database. The electronic Database can provide the system outputs in a summary, checklist, table, letter of medical necessity, or other appropriate format. The system output(s) can also include target literature and/or clinical support resources for the submission that has been found useful in the approval process. The user then reviews the patient's information to comply with the electronic Database system outputs and submits the materials and information to the insurance company.

The electronic Database may also provide an output protocol specific to the insurance company where the protocol defines what steps make the submission more efficient and effective (the how and when of the submission). In some aspects, the output protocol may also include timing information on how and when to monitor approval, and if declined, how and when to move forward on an appeal.

In some embodiments, the results of any one submission to an insurance company is used to update the electronic Database for future use, such that the electronic Database provides the most updated system outputs and protocols for any one specific insurance company.

In another embodiment, the system can populate output information that is specific to the patient, or can provide a template letter where the user inputs the system outputs with the patient's specific information.

DETAILED DESCRIPTION

Figure 1:
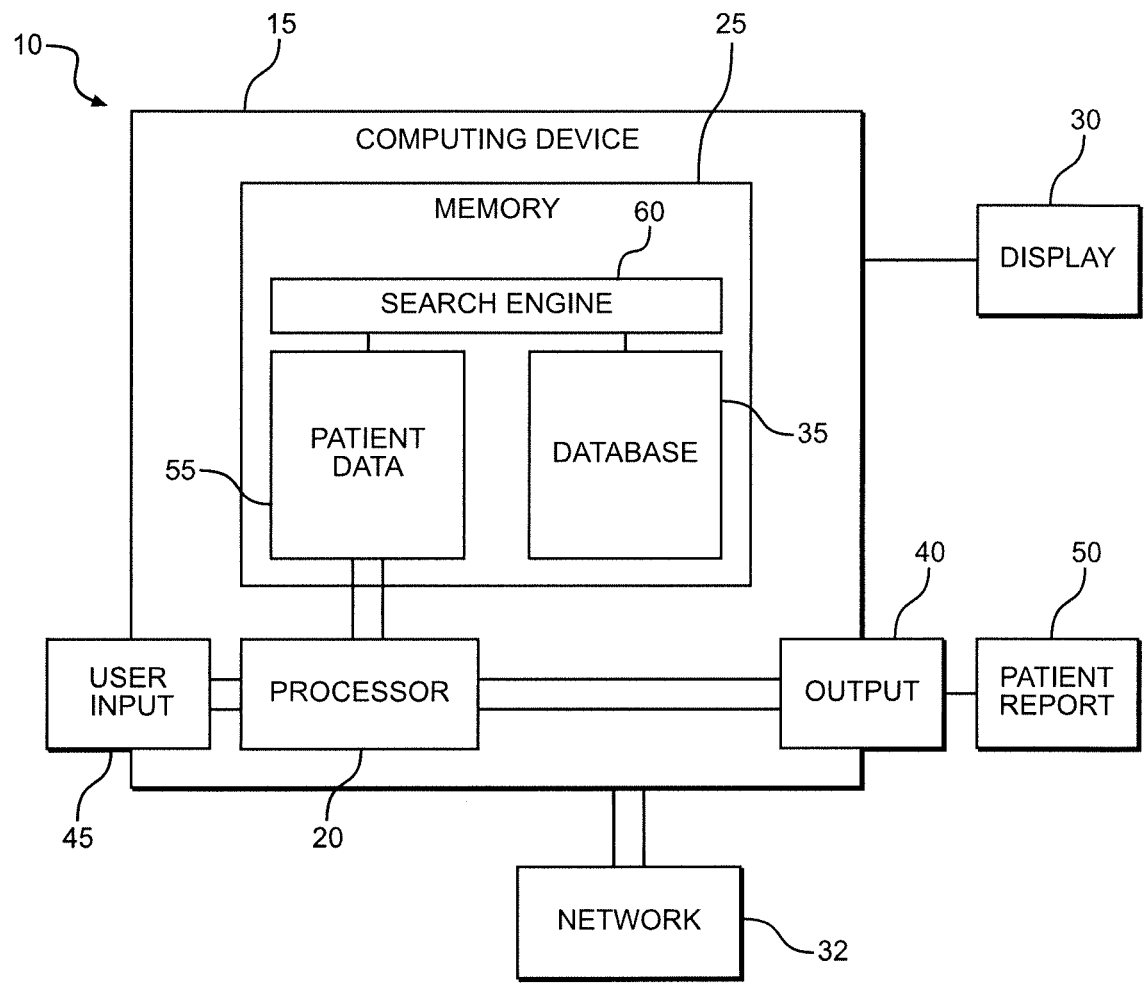
FIG. 1 depicts a network system including a computing device with a memory for storing a database.

Embodiments herein relate to systems and methods for facilitating insurance coverage. Each insurance company has its own requirements for finding a medical procedure, treatment or medicine necessary, and therefore covered by a policy. Embodiments herein provide systems and methods designed to provide outputs to assist health care providers in more efficiently and effectively pursuing coverage of a medical procedure, treatment or medicine from a specific insurance company. If the correct system outputs are not provided or addressed to an insurance company, data has shown that the requested procedure, treatment or medicine will likely be denied coverage. In some embodiments, the target criteria are further supplemented with supporting literature, and other materials, to further enhance a finding of coverage by the insurance company.

Embodiments herein have been designed to assist health care providers in efficiently and effectively pursuing coverage for a patient's requested procedure, treatment or medicine. Embodiments generally rely on systems and methods that identify user inputs specific to the patient's medical situation and insurance company. These user inputs allow for a search and analysis of an electronic Database where the electronic Database outputs specific information considered medically necessary for the insurance coverage to be approved.

Typical embodiments include user inputs used to search, by a search engine, an electronic Database to identify system outputs for facilitating coverage of a medical procedure, treatment or medicine. In some aspects, the electronic Database is searched using one or more user inputs, including: the patient's insurance provider, the medical procedure, treatment or medicine, and the patient's diagnosis. The electronic Database is searched and data analyzed to output information considered highly useful in facilitating coverage for the requested medical procedure, treatment or medicinal. In some aspects, the system outputs are populated into a letter (Letter Of Medical Necessity, "LOMN") used by the medical health care provider to submit to the insurance company. The LOMN represents an efficient and effective submission of material to the insurance company. As referred to herein, a LOMN is a document in support of why a treatment is medically necessary for a patient by specifically addressing information necessitated by the insurance company, as is described in greater detail below.

In embodiments herein, the electronic Database is searched using user inputs tailored to the insurance company and patient's proposed medical procedure, treatment or medicine. In other embodiments, the electronic Database is searched using user inputs tailored to the insurance company, patient's medical procedure, treatment or medicine, and the patient's diagnosis. In still other embodiments, the electronic Database is searched using user inputs tailored to the insurance company, patient's proposed medical procedure, treatment or medicine, the patient's diagnosis, and the patient's personal health information. Finally, in some embodiments, the user inputs can include information teased out of the patient's insurance policy. Note that a patient's personal health information may include clinical notes, patient's history, prior procedures, treatments and medications, patient allergies, etc.

However, it is envisioned that other inputs relevant in identifying Database system outputs are within the scope of the embodiments described herein. For example, in some aspects, higher detail user inputs, termed "high detail user inputs" specific for particular medical procedures, treatments or diagnosis may be identified as helpful for the electronic Database search, as is discussed in greater detail below.

Definitions

The following definitions are provided to further enhance the understanding of the description herein:

Supplemental literature within the scope of the present disclosure includes: journal articles, news articles, white papers, position statements, society recommendations, regulatory information, presentations, pamphlets, medical videos, pictures, book chapters, medical policies, and other like materials, related to the relevant diagnosis, medical procedure, insurance company and insurance company policy. A bundle or combination of supplemental literature can be developed for user inputs, for example, a series of articles that relate to the clinical outcome of a osteochondral allograft transplantation useful for insurance providers that have shown a higher likelihood of coverage where such literature is provided. Any bundle of supplemental literature is specific to a specific insurance company. Electronic Database literature system outputs can be updated and tailored for each particular insurance company based on positive and negative reimbursement claim outcomes and are tied to the specific diagnosis and patient indications used to demonstrate that the procedure, treatment or medicine is effective. Electronic Database literature is also updated based on insurance company changes to policy requirements, as well as, based on new clinical findings, new publications, and new recommendations written by various authoritative societies (e.g., the American Society of Diabetes, Arthritis Society, American Cancer Society, National Cancer Society, American Association of Pharmaceutical Scientists, etc.).

Diagnoses user inputs within the scope of the present disclosure include: cerebrovascular disease, cardiovascular disease, heart attack or failure, hypertension, diabetes, arthritis, osteoporosis, renal failure, Alzheimer's disease, depression, cancer, liver disease, liver sclerosis, multiple sclerosis, hepatitis, amyotrophic lateral sclerosis, cataracts, wound repair, burn repair, osteochondritis dissecans, degenerative chondral lesions, traumatic chondral injury, osteonecrosis, fracture, failed osteochondral allograft, bone augmentation, spinal fusion, and other known medical conditions.

Healthcare insurance company (or provider) user inputs within the scope of the present disclosure include: AETNA, BLUE CROSS BLUE SHIELD, CIGNA, UNITED HEALTHCARE, HUMANA, ANTHEM, CENTENE CORPORATION, HEALTH NET, WELLCARE HEALTH and other like companies. The term Insurance company herein includes other third-party payors, private payors, or government payors. Each insurance provider may have an unique policy for a particular medical procedure, as is discussed in more detail throughout.

Medical procedures, treatment and medicine user inputs within the scope of the present disclosure include: medical testing, medical exams, diagnostic testing, medications, surgical procedures (both in- and out-patient hospital procedures), also including implants and transplants, psychological exams and studies, pharmaceuticals, rehabilitation/therapies, prosthetics, and other like health care issues. Any medical procedure, treatment or medicine that requires insurance company approval is within the scope of the present disclosure. With regard to medical implant input criteria, for example, the criteria may include bone implants in the elbow, shoulder and humeral head, ankle, talus, patella, trochlea, femoral condyle, tibial plateau, hip, jaw, spine, and other like sites. Note that each medical procedure, treatment or medicine may include higher detail user inputs.

Implementing the Database

Embodiments herein include a network system 10 shown in FIG. 1 for implementing aspects of the methods herein. The network system includes a server or other like computing device 15. The server having at least a processor 20 coupled to a memory 25 and display 30. The memory can be a Non-Volatile ("NV") memory, like a flash memory, or a Random Access Memory ("RAM"), Read Only Memory ("ROM"), magnetic disc, optical read disc and the like.

Other aspects of the memory can include Direct Access Storage Device ("DASD") or other peripheral device accessible by the network.

The network server is configured to connect to any number of remote computing devices, where each remote commuting device further includes a processor, memory and display. Each of the servers and processors is capable of running software to facilitate the embodiments described herein. The server is typically coupled to the remote computing devices by a local network, wide area network, Internet, wireless networks (including WiFi), or other like networks 32. The server can also be configured to connect to any number of other servers and systems. Each additional server may have its own database and software useful to the embodiments herein. The servers can be coupled together using various security measures, such that the data and services can be exchanged securely.

The servers and remote devices can include computer readable medium having executable instructions. The readable medium can include disc drives for readable data storage media, or medium such as RAM and ROM. It is also envisioned that the readable medium includes non-volatile, optical, or any other type of memory storage.

Systems and Methods

Many of the medical procedures, treatments and medicines performed or used in the United States require approval from the patient's insurance provider in order for the medical provider to be reimbursed or paid by the insurance company, i.e., covered. Also within the scope of the present disclosure are cases where the insurance provider does not require approval for a procedure, treatment or medication, but then denies that procedure, treatment or medication due to the patient's policy. As such, the terms "approval" "pre-approval" and "prior-approval" for purposes herein include the preceding situations, and include any request of an insurance company to financially cover a medical procedure, treatment or medication for a patient.

Covered medical procedures, treatments or medicines are often termed as meeting the insurance companies' medical necessity criteria and guidelines. Insurance companies provide criteria and guidelines that patients must address and comply with for the procedure, treatment or medicine to be considered "medically necessary", and therefore acceptable for reimbursement. Identification of an insurance companies' criteria and guidelines for any particular procedure, treatment or medicine is very burdensome on the health care provider and patient. In addition, insurance companies differ in what criteria and guidelines they use to define coverage. For example, the system outputs that define criteria to obtain authorization of a medical procedure for Blue Cross Blue Shield often differs from the system outputs that can result in authorization of the same medical procedure for Cigna. As can be imagined, for example, if the system output for Blue Cross Blue Shield is submitted to Cigna instead, the prospects for authorization are reduced, and the efficiency of the approval process significantly impaired.

Embodiments herein include methods and systems for identifying and outputting the information and guidelines to efficiently and effectively assist health care providers in obtaining authorization for a proposed patient medical procedure, treatment or medicine based on one or more inputs. In all embodiments, the user inputs include the insurance company where coverage is sought and the medical procedure, treatment or medicine for what coverage is being requested. In other embodiments, the user inputs may include the patient's diagnosis. In still other embodiments, the user inputs may include the patient's health information (clinical notes, patient history, prior procedures, treatments and medications, results of diagnostic tests, patient allergies, etc.). And in still other embodiments, the user inputs may include factors found in the particular policy owned by the patient.

Embodiments herein provide an electronic Database 35 specific for system outputs 40 to increase the efficiency of a healthcare provider in applying for prior-authorization, as well as in facilitating the effectiveness of a targeted medical procedure, treatment or medicine being reimbursed. As noted above, the electronic Database 35 is driven by user inputs specific to the insurance company and medical procedure, treatment or medicine, and in some embodiments, the diagnosis, medical information, and/or policy.

The one or more user inputs to the electronic Database results in system outputs that increase the efficiency of the healthcare provider (or other user) and patient in preparing and submitting information for approval, and facilitates the possibility of approval for coverage from the insurance company.

It is also envisioned that the embodiments herein may provide for greater efficiency for insurance providers, where a more effective approval request allows for fewer appeals and more efficient use of insurance provider personnel and resources.

In one embodiment, software configured to analyze the electronic Database 35 and submits one or more system outputs 40 that addresses the particular user inputs 45. The electronic Database system outputs 40 may be provided in any format found useful to the health care provider, for example, a summary document, a bullet point listing, a checklist, a table, an excel sheet, etc. In some aspects, system outputs may be prioritized by the electronic Database into different levels or categories of importance: for example, from most to least important to include in a submission, or information that must be included in submission, useful to include in a submission, not necessary but if known to include in a submission, and the like. In addition, the software and Database can provide a system output as well as an alternative system output for submission to the insurance company. For example, the system output is submission of MRI results on the osteochondral defect, in the alternative, where an MRI has not been performed, the system output is to submit results of an arthroscopy examination. It is also envisioned that the output may include warnings or alerts for the health care provider, such as an alert that if a particular system output is not met, the likelihood of coverage is negatively affected, or alerts for submitting prior-approval information by a specific date, when to follow-up with the insurance provider, that a user is missing an item in the submission, etc.

In another embodiment, the electronic Database 35 results in outputting a patient report 50 such as a personalized LOMN that addresses the specific information defined by the system outputs including the criteria of the insurance provider and insurance provider policy, as well as the patient's information. The letter is designed for increasing the efficiency and effectiveness, particularly related to timing, of obtaining positive results for insurance company approval and reimbursement. The LOMN is designed to improve the efficiency for the health provider in submitting for approval to the insurance company by providing relevant paperwork, resources and information typically tied to the patient's policy. The LOMN may include some or all system outputs that correspond to the patient's or users' inputs. Although not always the case, having the patient's personal health information such as indications as one of the inputs is helpful in the LOMN submission, for example, could allow for the submission of clinical support (literature, publications, etc.) related to specific patient indications.

Embodiments herein provide methods and systems for facilitating approval of a medical procedure, treatment and/ or medicine claim, and if unsuccessful, facilitate a reverse of a denial by the insurer. Benefits of facilitating both the approval, and where necessary, an appeal of a medical procedure, treatment or medicine, include: insurance provider authorization and payment to perform the procedure, decreased burden in time and cost on the patient to obtain insurance approval, reduced time and cost for the medical provider, reduced waiting time for the patient to receive the medical procedure, and improved quality of life for the patient given the faster access to treatment.

As noted above, embodiments herein are implemented through computing devices. For purposes of this disclosure, a patient in need of a medical procedure contacts a user of the method and system embodiments described herein (referred to herein as the user). A typical user herein is the health care provider where the patient will have the medical procedure, treatment or medicine performed or provided. A health care provider herein refers to any employee or independent contractor at the provider, including personnel authorized to make insurance submissions, including doctors, nurses, hospital staff, administrative assistants, secretaries, billing specialist, accountants, etc. Another typical user is a third party company that assists with insurance approval.

In some embodiments, the user then obtains documentation or other patient data 55 from the patient including, the identity of the patient's insurance company, the identity of the patient's insurance company policy, any relevant medical referrals, the patient's medical history, the patient's clinical notes, including all clinical information relevant to the medical procedure, any medical dictations relevant to the procedure, treatment or medication, relevant results of diagnostic testing, any prior treatments, the patient's diagnosis and the patient's diagnosis if the medical procedure, treatment or medicine is approved, as well as the patient's diagnosis if not approved. Once this information is obtained by the user, an electronic Database is searched using the software search engine 60 appropriate for the embodiments herein, based on the obtained input information, to result in system outputs that best facilitate approval of coverage by the insurance company.

In one embodiment, the patient's insurance company is input into the electronic Database. Inputs may be through drop down list box or through search fields. For Example, an insurance provider selection will result in a drop down list box having AETNA, BLUE CROSS BLUE SHIELD, CIGNA Aetna, etc. Although not limited by sequence of input, a selection of the patient's insurance company may result in a patient's policy type for that insurer to be input via a drop box or search field. Once the insurance company input is entered, the patient's requested medical procedure, treatment or medicine is input by a drop box or search field. In some aspects, the selection of a medical procedure, treatment or medicine will result in a drop box or search field for inclusion of a more detailed input submission. For example, if the medical procedure, treatment or medicine is a medical implant, a new drop box having a list of implant sites will drop down, or if the medical procedure, treatment or medicine is skin cancer, the drop box list may include the type of skin cancer and the location of the cancer (scalp, neck, torso, etc.). In still another aspect, the patient's diagnosis may be input, and like the above, a more detailed input may be used, including drop boxes for diagnosis if the medical procedure, treatment or medicine is not approved. Finally, input drop boxes (or search fields) may be completed that include patient specific information and indications, for example, the patient's age, BMI, prior surgical procedures, allergies, patient history, clinical notes, dictations, results from diagnostic tests, and the like. In addition, where insurance coverage has previously been denied for the patient, inputs may include a drop box that lists the reason(s) the insurance was originally denied, as well as inputs for any specific reasons provided by the insurance company for why the coverage was denied. Requested input information will update based on policy information and responses from payors.

Based on the totality of the user inputs, the electronic Database, as described below, is searched and analyzed, and a set of specific system outputs provided. The outputs allow for an efficient and effective preparation and submission of information and materials to the insurance company for a finding of medical necessity. In some aspects, the system outputs are presented as a summary document, checklist, bullet list, or other format that assists the user in the preparation and submission of materials during the authorization process. In some aspects, the outputs are populated into a LOMN. In some aspects, the outputs may include the specific protocols or steps for how to obtain approval from the insurance provider (the how and why of the submission).

Where the electronic Database uses the patient's insurance policy, the Database extracts the outputs for a specific insurance provider and policy such that the user can have immediate access to information. Input of the policy is particularly helpful, as policies are always changing and different between insurance companies. Inclusion of the patient's policy in the input, means that the outputs will be tailored to specific requirements for the patient and therefore further enhances the usefulness of the electronic Database. For example, in an extreme circumstance, the patient's policy may deem the medical procedure, treatment or medicine as experimental, necessitating additional procedural steps in the submission for coverage. Also, in another example, the system outputs are tailored to the patient information inputs. Based on the diagnosis and patient clinical information, the outputs can inform the user if the patient's policy will consider the procedure, treatment or medicine medically necessary. If the procedure, treatment or medicine is not medically necessary in the policy, the system outputs can provide supporting materials and information to demonstrate why the procedure, treatment or medicine should be considered medically necessary.

In some cases, system outputs include bundled literature to support why the medical procedure, treatment or medicine should be considered medically necessary. As noted above, the bundled literature may also be included with the LOMN submission or any other user submission to the insurance company.

In some aspects, the user then provides the system outputs to the target insurance company for the patient's medical procedure, treatment or medicine for approved. In some other aspects, the system can output additional processes or protocols that can assist the approval process with a specific insurance provider. For example, the system outputs may provide a follow-up letter or phone call timed and delivered every few weeks to the insurance company to identify any shortcomings that the insurance company has identified, or to encourage the insurance company to reimburse the insurance claim.

In still other embodiments, the user inputs to the electronic Database result in a tailored protocol for each insurance provider. The tailored protocol details how and when to submit materials to an insurance provider. For example, a protocol may be electronically output for a specific insurance company and medical procedure where the steps include: step 1: collect all patient information of clinical importance; step 2: communicate with specific insurance company in order to submit materials, for example, go to the insurance companies website for submission of materials (link can be provided by electronic Database output); step 3: call number, e-mail or other communication modes provided by the insurance company to check on approval in two weeks; step 4: request status of submission from the insurance company every 30 days (or other set amount of time); and step 5: if not approved, provide a method and timeline for follow up, and provide appeals process information specific for follow-up request.

In more detail, a patient in need of a medical procedure, treatment or medicine can include a patient in need of most surgical procedures, medical testing, diagnostic testing, rehabilitation, physical therapy, prosthetics, and use of medical specialist. In addition, most pharmaceuticals, particularly for multi-use or chronically required drugs, also require pre-approval from the patient's medical insurance provider, and medications/pharmaceuticals are within the scope of the embodiments herein.

A user of the methods and systems herein may include the patient, a health care provider which will perform, or dispense, the medical procedure, an advocate for the patient, e.g., friend, family member, medical association, etc., a third party who assists the health care provider with reimbursement, or any other individual or group having access and need of using the systems and methods as described herein. In typical aspects, the user will have proper certification/regulation to access the patient's information. The user will access the methods and systems as described herein, typically through a network system. Note that in typical embodiments, the user is a health care provider where the procedure will be performed.

An electronic Database within the scope of the present disclosure is created, updated, and stored on the network system as described herein. The electronic Database is searched using software having one or more user inputs disclosed herein to provide system outputs for use in preparing and submitting the information required for approval of a medical procedure. In some cases, the system outputs are used to create a checklist or summary, and in other cases, the outputs are used to create a LOMN.

As noted above, software implemented user inputs for searching the electronic Database can include: the insurance provider company, patient's requested medical procedure, treatment or medicine, the patient's insurance policy, and the patient's medical diagnosis. In some embodiments, the patient's more specific medical requirements can be included as detailed inputs, for example, if the medical procedure is an implant, the location and type of implant can be included as an input. In addition, in still other embodiments, the electronic Database also takes into account inputs specific to the patient's information or indications, i.e., if the patient had prior surgeries, diagnostic test results, clinical notes, patient's BMI, patient's age, etc.

The electronic Database is searched using the user inputs to locate system output information that increase the efficiency and effectiveness that the medical procedure, treatment or medicine be considered necessary. In some cases, the system output information provides the criteria and required documentation defined by the insurance policy. In addition, system outputs can provide resources to support why a procedure, treatment, or medicine in combination with a diagnosis should be considered medically necessary. System outputs for a specific insurance company, insurance company medical policy, diagnosis and/or medical procedure, treatment or medicine may include, but are not limited to, any one or more of the following: what type of patient examination and documentation is most likely to result in approval, what type of diagnosis is most likely to result in approval, what patient symptoms will most likely result in approval, what types of failed treatments has the patient tried that will most likely result in approval of the requested medical procedure, whether inclusion of alternative treatments will likely result in approval, additional physical findings that will result in approval, what age groups are most likely to result in approval of the requested medical procedure, what range of patient BMI will most likely result in approval of the requested medical procedure, whether it matters or not that the patient is willing to comply with a rehabilitation program after the medical procedure is performed, whether the patient is allergic to particular classes of pharmaceuticals, and what supporting bundled literature is most effective at resulting in the medical procedures, treatments or medicines approval. With regard to the system outputs for a type of patient examination and documentation, the electronic Database can include whether inclusion of documentation of the patient's history, physical exam, radiology reports, mental health exams, MRI results, specialist findings, clinical/literature support for the patient's diagnosis/indications, and the like, are useful for facilitating approval.

In one embodiment, user inputs in the software are utilized to filter an electronic Database based on the insurance company, and requested medical procedure, treatment or medicine and diagnosis, such that optimized or facilitated system outputs are disclosed to the user. In another embodiment, user inputs are used to filter the electronic Database based on all of the inputs available to the user, including: insurance company, patient's policy, medical procedure, treatment or medicine (including any detailed information), diagnosis, and patient's information (including clinical information), such that optimized or facilitated outputs are disclosed to the user.

Based on the user inputs, an output(s) is established, where each output results in facilitating insurance company approval. In one aspect, the system output can be a checklist of materials and information useful for submission to that specific insurance provider. System outputs can also include resources (clinical support and literature) to support why the procedure, treatment or medicine should be considered medically necessary. In some alternative embodiments, system outputs can include protocols or steps for submitting for an approval from a specific insurance provider company. Protocols or step outputs further enhance the submission by providing the best timing, tools and sequences of events for a submission to a particular insurance company, where these protocol or step outputs increase the likelihood of approval. For example, an output protocol may include the timing of when an optimal submission is provided to a particular insurance company, i.e., within a month of the requested procedure, within a week or the suggested procedure, within a year of the last procedure, etc. Electronic databases are continuously or periodically updated to strengthen and modify outputs that result in approval.

In one aspect, the software and electronic Database provide the most useful information and materials necessary to support the payment of the patient's medical procedure. As noted above, the system outputs may also include support documentation.

Electronic Database embodiments have been developed through an extensive evaluation of user prior-authorization submissions, insurance company policies, and patient policies as related to specific medical procedures, treatments and medicines, and in some cases, patient diagnosis. Databases are populated and configured to include fields that provide or facilitate the approval process specific to an insurance company and the insurance company healthcare policies. Each field has an association with the particular insurance company, the particular medical procedure, treatment or medicine, and, in some cases, the particular diagnosis. The electronic Database has been populated with the findings that result in or facilitate a finding of approval, and include a significant number of entries. For example, for a medical implant (medical procedure), numerous combinations of system outputs have been included in the Database that have resulted in an increased likelihood for a specific insurance company finding a procedure, treatment or medicine covered. The electronic Database search allows for the system outputs that enhance the efficiency and effectiveness of the submission.

An illustrative software-based electronic Database search for a patient in need of an osteochondral implant may result in an insurance company and policy specific output of: the patient's history and consultation note(s), the patient's grade defect and surrounding cartilage, the last physical exam for stability, whether there is closure of growth plates, the reason(s) the patient isn't a TKA (total knee arthroplasty) candidate or a candidate for other procedure, the reason(s) for requested procedure and treatment, and the patient diagnostic radiology reports. The documentation may include: prior treatment and responses and MRI testing results. The output may be in the form of checklist, that the user reviews and complies with during submission to the insurance company. As noted above, the outputs may be graded or prioritized or may provide alternative outputs. For example, the checklist may include a box for MRI testing results, or in the alternative, arthroscopy results.

In addition, with regard to illustrative system outputs (as dependent on the insurance company), an implant procedure may include: type of examination, cartilage defect description, patient symptoms, prior surgical and non-surgical treatment, joint stability and alignment, joint health and surrounding cartilage, patient age, patient body mass index (BMI), and patient willingness to comply with rehabilitation.

Figure 2:
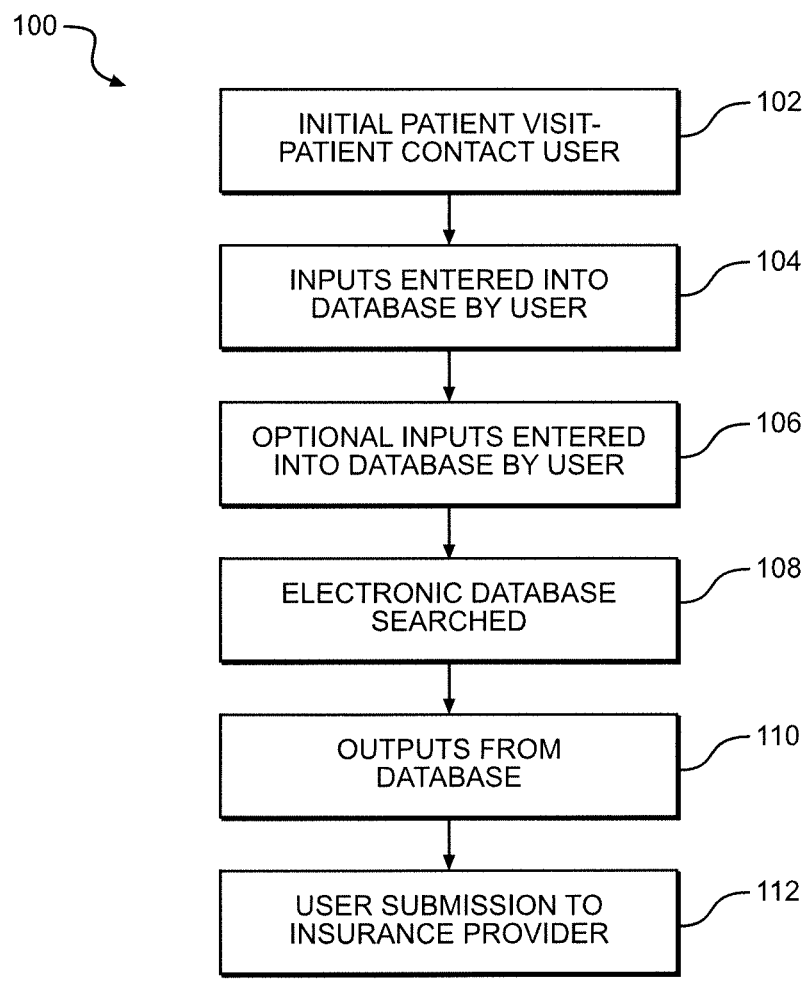
FIG. 2. depicts a flow chart of an illustrative method in accordance with embodiments.

Referring to FIG. 2, an illustrative flow chart of a reimbursement method is provided 100. All operations of the method include a user input related to insurance company, for example, BLUE CROSS BLUE SHIELD, and a medical procedure (or treatment or medicine) that requires approval, for example, medical implant. Inputs may also include the patient diagnosis, patient specific information, and patient insurance policy. It is envisioned that the electronic Database will include system outputs for use with any combination of inputs: insurance company, policy, medical procedure, diagnostic combination and patient specific information.

In operation 102, a patient in need of embodiments herein contacts a user. The user typically operates the software operations via a network server. In operation 104, the patient's insurer, and requested medical procedure, treatment or medicine, are input to the system by the user. In operation 106, the patient's diagnosis and personal health information are input (may be optional). In operation 108, an electronic Database, in accordance with embodiments herein, is searched using the above inputs, resulting in a finding of system outputs for use in facilitating an efficient and effective approval of the medical procedure 110. In operation 112, a submission is made to the insurance provider including the appropriate outputs.

As noted above, the electronic Database has been developed to include system outputs that provide for more efficient approval and increased likelihood of approval by the insurance company. As such, the Database has been developed using data mining techniques to update and tailor the output criteria found to increase the likelihood for the particular insurer, medical procedure, diagnosis to be approved. In some cases, the electronic Database is also tailored using information obtained from denials, and the reason for denials, of patients by insurance providers. In some embodiments, two inputs are required for a search, in other aspects, three inputs are required for a search, in other embodiments, four or five inputs are required for the search. In still other embodiments, the number of inputs can be six, seven, eight, nine or any number that facilitates the output of useful material for the submission to the insurance provider. Inputs to the software direct the search to identify the output criteria most useful in obtaining approval.

For each insurance company, based on each medical procedure, the Database includes the updating combination of outputs that have been shown to result in a streamlined approval process for an insurance claim. Outputs may further include additional sub-information or detail. For example, if the requested medical procedure is a medical implant to the shoulder, the Database could provide outputs that will facilitate insurance approval such as the size, location and type of osteochondral defect. These output combinations have been shown to differ between insurance companies and policies, and a user needs to highlight and discuss how the specific patient seeking insurance approval meets the specific outputs.

Database embodiments herein are updated periodically with additional data. In one aspect, the database is constantly being updated if the insurance was approved or denied, and the reason or reasons for the approval or denial. The information would be used to update the outputs for a later user of the system and methods disclosed herein. So for example, a patient is denied coverage by an insurance company because the approval information did not include results for an MRI. The electronic Database is updated for that insurance provider and medical procedure that an MRI examination is highly suggested as part of the submission in order to obtain approval. The data can be delivered as a prioritized output or as an alert for the next user.

Illustrative LOMN

Each user, based on the user inputs, may have an electronic Database generated LOMN, as described herein. Generated letters include a request for authorization for a target medical procedure. The letter sets out the Database provided system outputs and describes how the patient meets the insurance provider's approval criteria. As discussed above, these outputs are specific for each insurance company and can include: the patient's history, types of examination, symptoms, current condition, treatment rationale that will be covered to support the medical necessity of the medical procedure. The letter can also indicate that supporting materials have been provided, including supporting medical literature, or bundled literature, as generated by the Database to support that the medical procedure, for example, be considered medically necessary. In this embodiment, the electronic Database correlates and provides literature to support a medical procedures finding of necessity based on the patient's specific findings (single-bypass as opposed to double by-pass or defect in shoulder versus defect in ankle, etc.), or based on the users experience and history of treating patients with similar or identical inputs.

In some aspects, the letter is a template letter used to support why the particular procedure, treatment or medicine is considered medically necessary. The template can be derived from system outputs that result from the users experience and history of treating patients with similar or identical inputs. In other aspects, the letter can also include a summary optimized for a specific patient's approval, and may include, for example: details of the patient's medical history, current diagnosis, duration/degree of symptoms, summary of past failed treatments and the patient's age. The letter would then include the health care givers examination and diagnosis by describing, for example, an examination of the joint stability and alignment, the examination of the defect (MRI for example), the description of the defect, a description of surrounding cartilage, and the status of the meniscus.

The following examples are illustrative and not meant to narrow the scope of the embodiments.

EXAMPLES

Example 1: Conventional Methodologies for Reimbursement

An analysis of some 28 end-user/medical provider claims for reimbursement related to medical implants is provided. Each of the 28 events was reviewed for a prior-authorization process, and where necessary, an appeal process, as well as frequency of denials for different graft types. The results of the review indicate that end-users and health care providers have inconsistent claim reimbursement procedures, and that denials can be influenced by the graft type.

With regard to authorization, only 21/28 (75%) of the end-user/medical providers knew that prior-authorization was required for claim reimbursement, and only 14/28 (50%) of the end-users/medical providers had a predetermined process for submitting a claim for prior-authorization. Finally, only 7/28 (25%) of the end-users/medical providers included one or more of patient criteria, letters of medical necessity or literature in their attempt at prior-authorization.

With regard to the appeals process, the end-users/medical providers that required an appeal to a claim, also showed a surprising range of procedures. Fewer than half the end-users/medical providers in need of an appeal provided any one of the following: literature, patient letter, or a letter of medical necessity. Further, less than 20% of the appeals included any follow-up with the insurance provider.

Finally, denial of these insurance claims indicated that denial was greatest for implants required for the elbow and shoulder, but lowest for the ankle.

This Example indicates that end-users and health care providers use inconsistent, and sometimes no procedures, to attain prior-authorization for a medical procedure, or to appeal a negative decision by an insurer. Inconsistency, and information submitted to the insurance company, all have an effect on reimbursement, indicating that a consistent procedure, tailored to the medical condition, and the patient's insurer would improve the chances of obtaining approval for a claim.

Example 2: Output of Specific Medical Policy

Each insurer may have a specific medical policy that defines the information and guidelines for defining medical necessity. The policy below provides an illustrative policy for Insurer X:

| Policy Number: | Surg.00093 |
|---|---|
| Status | Reviewed |
| Current Effective date | Oct. 4, 2016 |
| Last Reviewed | Aug. 4, 2016 |

This document addresses treatment of osteochondral defects of the knee, ankle and other joints using the following procedures or devices:

Autologous chondrocyte transplant (ACT)
Minced cartilage repair
Osteochondral allograft
Osteochondral autograft (OATS/mosaicplasty)
Resorbable synthetic bone filler materials
Note: Please see the following related document(s) for additional information:
Surg.00011 Allogeneic, Xenographic, Synthetic and Composite Products for Wound Healing and Soft Tissue Grafting
Trans.00015 Meniscal Allograft Transplantation of the Knee
Position Statement
Medically Necessary
Note: Members must meet the disease specific criteria, as well as the general criteria as set forth in this document for the specific procedure to be considered medically necessary.

Autologous chondrocyte transplantation ("ACT"), also known as autologous chondrocyte implantation ("ACI"), to treat cartilaginous defects of the knee is considered medically necessary when all of the following criteria are met:

1. Inadequate response to prior surgical therapy to correct the defect;
2. Size of the cartilage defect is greater than or equal to 1.5 cm2 (i.e., length×width) in total area;
3. The defect involves only the cartilage and not the subchondral bone, unless ACT is being used to treat osteochondritis dissecans associated with a bony defect 10 mm or less in depth which has failed prior conservative treatment. Lesions due to osteochondritis dissecans associated with a bony lesion great than 10 mm in depth must also undergo corrective bone grafting;
4. No known history of allergy to the antibiotic Gentamicin;
5. No known sensitivities to bovine cultures;
6. Condition involves a focal, full thickness (grade III or IV) isolated defect of the knee involving the weight bearing surface of the medial or lateral femoral condyles or trochlear region (trochlear groove of the femur) caused by acute or repetitive trauma; and
7. All criteria listed in the "General Criteria" section below are met.

Osteochondral allograft transplantation to treat cartilaginous defects of the knee is considered medically necessary when all of the following criteria are met:

This information is reviewed and additional input criteria identified. Where a policy included in the review of inputs, a LOMN may be generated rather than a checklist or other summary document.

Example 3: Illustrative LOMN

As a result of the Database system output, a template letter of necessity is generated including provider specific and patient specific criteria:

I am writing this letter to request pre-authorization for John Doe to perform an osteochondral allograft transplantation surgery. This letter provides information regarding the patient's medical history, current condition, diagnosis, and treatment rationale to support the medical necessity for an osteochondral allograft. This submission also includes all medical records and clinical notes, as well as, the supporting medical literature.

John Doe is a 35 year old male who first presented to my care in June of 2015. He described progressive, unrelenting and debilitating pain in his right knee since that time and has been in debilitating pain for over 6 months.

I performed a diagnostic arthroscopy to evaluate the status of his knee. A large lesion was found of his right lateral condyle with an estimated size of (2.2 cm×1.8 cm)4 cm2. He suffers from osteochondritis dissecans with associated avascular necrosis of the right knee. The defect is unipolar and discrete on the medial femoral condyle. The surrounding cartilage and menisci are normal with no signs of degeneration or osteoarthritis. The physical examination showed normal joint alignment and knee stability.

Example 4: Input Summary, Provider and OCA Information

The following example provides an illustrative user input for a provider and OCA information:

|  | Select the Following |
|---|---|
| Insurance Provider | AETNA |
|  | BLUE CROSS BLUE SHIELD |
|  | CIGNA |
|  | HUMANA |
| State | Colorado |
|  | Georgia |
|  | New York |
|  | Texas |
| Diagnosis | Osteochondritis dissecans |
|  | Degenerative chondral lesions |
|  | Traumatic chondral injury |
|  | Osteonecrosis |
|  | Facture |
|  | Failed osteochondral allograft |
| Graft Location | Femoral condyle |
|  | Tibial Plateau |
|  | Patella |
|  | Trochlea |
|  | Talus |
|  | Elbow |

Example 5: System Output Summary of A Medical Policy

The following example provides considerations for the information important for an insurer and policy, note that the outputs below result from the electronic Database embodiments as described throughout:

| Criteria | Specific or Sub-Criteria to be Considered Medically Necessary by Insurer X |
|---|---|
| Type of Examination | Arthroscopy or MRI examination results detail the size, location, and type of osteochondral defect |
| Cartilage Defect Description | Acute or repetitive trauma |
|  | Defect is located on weight bearing surface of MFC, LFC, or trochlear groove |
|  | Defect is focal and full thickness (grade III or IV), unipolar, single, discrete |
|  | Defect Size is ≥ 2 cm$^2$ in total area (length × width) |
| Patient Symptoms | Persistent symptoms of disabling localized knee pain for at least six months |
| Prior Surgical and Non-Surgical Treatment | Failed conservative treatment |
| Knee Stability and Alignment | Knee is stable with functionally intact menisci and ligaments and normal alignment |
| Joint Health and Surrounding Cartilage | Normal joint space, no infection, inflammation, or OA, no cancer in limb |
|  | Normal surrounding cartilage (<grade II) no kissing lesions |
| Patient Age | Adult, skeletally mature |
| Patient BMI | ≤35 |
| Patient Willingness to Comply with Rehab | Patient will comply with postoperative weight bearing and rehab |

Example 6: Illustrative Output of Required Documentation

The following example provides an illustrative listing of required documentation for an insurer X for a patient in State Y having been diagnosed with medical procedure Z.

| Required Documentation by Insurer X |
|---|
| History and consultation notes |
| Grade defects and surrounding cartilage |
| Physical exam for stability |
| Closure of growth plates |

| Required Documentation by Insurer X |
| --- |
| Prior treatment and responses
Reason patient isn't TKA candidate
Reason for requested procedure and treatment
Diagnostic radiology reports |

Example 7: Output of Supporting Literature

The following example provides an illustrative listing of supporting literature for a patient diagnosis at a target site for an insurer X.

| Supporting Literature |
| --- |
| Bugbee et al., Osteochondral Allograft Transplantation in Cartilage Repair: Graft Storage Paradigm, Translational Models, and Clinical Applications, J of Ortho Res, 2016, 31-38
Bugbee et al., Bipolar fresh osteochondral allografting of the tibiotalar joint, J Bone Surg Am. 2013, 6; 95(5): 426-32
Makino et al., The effect of graft sizing on osteochondral transplantation, Arthroscopy, 2004, 20(8): 837-40. |

What is claimed is:

1. A computer-implemented method for facilitating reimbursement of a first medical procedure claim for payment from an insurance company for a medical procedure, involving one or more of an implant and a therapy, for a patient performed by a computing device having a software-based search engine and an electronic database, comprising:

receiving, from a computer operated by a user, patient data wherein the patient data comprises the insurance company, a policy, and the medical procedure;

identifying inputs from the patient data, wherein the inputs are selected from, demographic information, indications, the insurance company, the policy, and the medical procedure and further include type of examination, exam description, patient symptoms, prior surgical and non-surgical treatment, type of implant, one or more of joint and implant site stability, one or more of joint and implant site health, patient age, patient BMI, and patient rehabilitation involvement;

continuously updating the electronic database, the electronic database configured to provide outputs in a form of a specific patient criteria and indications, needed to show that the medical procedure is medically necessary, for the patient's approval for the first medical procedure claim based on a history of previous medical procedure claim submissions based on treating other patients with similar inputs to the patient and whether the previous medical procedure claim submissions were authorized by the insurance company;

searching, by the computing device and via the software-based search engine, the electronic database with the inputs, for the outputs that include the specific patient criteria and indications to facilitate a finding of an authorization for the first medical procedure claim wherein the outputs are provided as a document setting forth medical examination results of examinations conducted on the patient;

determining, by the computer device, which one or more of the outputs do not meet the specific patient criteria and then identifying pertinent clinical support data, medical literature, and expert opinions to address the one or more of the outputs that do not meet the specific patient criteria and still provide medical justification for the medical procedure;

receiving the outputs that facilitate the authorization for the first medical procedure claim and the pertinent clinical support data, medical literature, and expert opinions that address the outputs that do not meet the specific patient criteria;

determining an extent the patient meets the specific insurance company criteria and determining areas where the patient does not meet the criteria and providing pertinent information to support to why the medical procedure is still necessary;

providing, by the computer device, additional pertinent clinical support data, additional medical literature, and additional expert opinions that provide medical justification for the medical procedure when the insurance company has previously determined the medical procedure is not medically necessary;

automatically generating a report in the form of a letter of medical necessity including a request for the authorization of the first medical procedure claim that discloses the outputs specific to the insurance company of the patient which describe how the patient meets the insurance company's approval criteria, discloses the pertinent clinical support data, medical literature, and expert opinions addressing the outputs that do not meet the specific patient criteria, and discloses the additional pertinent clinical support data, additional medical literature, and additional expert opinions that provide medical justification for the medical procedure; and submitting the letter of medical necessity to the insurance company.

2. The method of claim 1, wherein:

the patient data is compiled from relevant insurance information, physician referrals, patient history, physician reports, medical imaging and clinical information.

3. A system for enhancing a patient's healthcare comprising:

a memory storing:

a patient's data, wherein the patient's data is compiled from the patient's insurance company, physician referrals, patient history, a medical procedure involving one or more of an implant and a therapy, and patient clinical information and further includes type of examination, exam description, patient symptoms, prior surgical and non-surgical treatment, type of implant, one or more of joint and implant site stability, one or more of joint and implant site health, patient age, patient BMI, and patient rehabilitation involvement; and a database configured to provide outputs in a form of a specific patient criteria needed and indications needed to show that the medical procedure is medically necessary for the patient's approval for a first medical procedure claim for payment of the medical procedure for a plurality of insurance policies, the outputs based on a history of previous medical procedure claim submissions relating to treating other patients with similar patient data and whether the previous medical procedure claim submissions were authorized by the insurance company, wherein the electronic database is populated with fields for facilitating reimbursement of the first medical procedure claim based on the data, wherein the database stores a series of insurance company specific outputs used for facilitating an authorization for the medical procedure, the system being configured to continuously update the electronic database;

a processor in communication with the memory, wherein the processor is configured to:

search, the database with the patient data for the outputs that include the specific patient criteria to facilitate the authorization for the first medical procedure claim, wherein the outputs are provided as a document setting forth medical examination results of examinations conducted on the patient;

determine which one or more of the outputs do not meet the specific patient criteria and then identifying pertinent clinical support data, medical literature, and expert opinions to address the one or more of the outputs that do not meet the specific patient criteria and still provide medical justification for the medical procedure;

receive the outputs that facilitate the authorization for the first medical procedure claim and the pertinent clinical support data, medical literature, and expert opinions that address the outputs that do not meet the specific patient criteria;

determine an extent the patient meets the specific insurance company criteria and determining areas where the patient does not meet the criteria and providing pertinent information to support to why the medical procedure is still necessary;

provide additional pertinent clinical support data, additional medical literature, and additional expert opinions that provide medical justification for the medical procedure when the insurance company has previously determined the medical procedure is not medically necessary;

evaluate the patient's data against the database to automatically generate a patient report; and a computer output that electronically provides the patient report in the form of a letter of medical necessity including a request for the authorization of the first medical procedure claim that discloses the outputs specific to the insurance company which describe how the patient meets the insurance company's approval criteria, discloses the pertinent clinical support data, medical literature, and expert opinions addressing the outputs that do not meet the specific patient criteria, and discloses the additional pertinent clinical support data, additional medical literature, and additional expert opinions that provide medical justification for the medical procedure such that the patient report allows for an enhancement of the patient's healthcare.

4. The system of claim 3, wherein the patient report is a checklist.

5. The method of claim 1, wherein one of the outputs is a description and size of a cartilage defect.

6. The method of claim 1, wherein the electronic database further includes policy coverage information, medical literature and clinical support data.

7. The system of claim 3, wherein the output further comprises supporting literature.

8. The system of claim 3, wherein the electronic database further includes policy coverage information, medical literature and clinical support data.

9. The system of claim 3, wherein the outputs include clinical support data.

10. The method of claim 1 wherein continuously updating includes continuously screening all specific indications and contraindications for each medical procedure for the specific patient criteria needed to be considered medically necessary.

11. The method of claim 1 wherein facilitating the authorization for the first medical procedure claim includes supporting an appeals process after a denial is received from the insurance company.

12. The method of claim 1 further comprising listing implants along with extent of coverage for each implant.

13. The method of claim 1 wherein the outputs specify a specific procedure for submitting one or more of the first medical procedure claim, an appeal, and the authorization for the first medical procedure claim.

14. The method of claim 3 wherein the outputs specify a specific procedure for submitting one or more of the first medical procedure claim, an appeal, and the authorization for the first medical procedure claim.

* * * * *